United States Patent
Chen et al.

(10) Patent No.: US 9,108,042 B2
(45) Date of Patent: Aug. 18, 2015

(54) DEVICE FOR STIMULATING NEURAL REGENERATION AND FABRICATION METHOD THEREOF

(75) Inventors: Fang-Chung Chen, Hsinchu (TW); Ming-Kai Chuang, Hsinchu (TW); Kim-Shih Tan, Hsinchu (TW)

(73) Assignee: National Chiao Tung University, Hsinchu (TW)

( * ) Notice: Subject to any disclaimer, the term of this patent is extended or adjusted under 35 U.S.C. 154(b) by 163 days.

(21) Appl. No.: 13/587,155

(22) Filed: Aug. 16, 2012

(65) Prior Publication Data
US 2013/0317582 A1    Nov. 28, 2013

(30) Foreign Application Priority Data
May 24, 2012    (TW) .............................. 101118472 A

(51) Int. Cl.
*A61N 1/05* (2006.01)
*A61F 7/12* (2006.01)
*H01L 51/42* (2006.01)

(52) U.S. Cl.
CPC ................ *A61N 1/0556* (2013.01); *A61F 7/12* (2013.01); *H01L 51/42* (2013.01)

(58) Field of Classification Search
CPC ........................................................ A61F 7/12
USPC ............................ 607/98, 114, 115, 116, 118
See application file for complete search history.

(56) References Cited

U.S. PATENT DOCUMENTS

| | | | |
|---|---|---|---|
| 4,308,868 A | 1/1982 | Jhabvala | |
| 5,030,225 A * | 7/1991 | Aebischer et al. | 606/152 |
| 6,366,802 B1 * | 4/2002 | Haber et al. | 600/474 |
| 7,058,455 B2 * | 6/2006 | Huie et al. | 607/116 |
| 2005/0021108 A1 * | 1/2005 | Klosterman et al. | 607/48 |
| 2006/0100679 A1 * | 5/2006 | DiMauro et al. | 607/94 |
| 2008/0300663 A1 * | 12/2008 | Blick et al. | 607/116 |
| 2009/0024182 A1 * | 1/2009 | Zhang et al. | 607/54 |
| 2009/0082832 A1 * | 3/2009 | Carbunaru et al. | 607/59 |
| 2010/0249877 A1 * | 9/2010 | Naughton | 607/54 |
| 2010/0292629 A1 * | 11/2010 | Dacey et al. | 604/8 |

* cited by examiner

*Primary Examiner* — Christopher D Koharski
*Assistant Examiner* — Jeremiah Kimball
(74) *Attorney, Agent, or Firm* — Mintz Levin Cohn Ferris Glovsky and Popeo, P.C.; Peter F. Corless; Steven M. Jensen

(57) ABSTRACT

The present invention provides a device for stimulating neural regeneration and/or neurite outgrowth and a fabrication method thereof. A photovoltaic component having a substrate, a first conductive layer, an active layer and a second conducting stacked in sequence is formed. The photovoltaic component is encapsulated by an encapsulant with a portion of the first conductive layer and the second conductive layer exposed from the encapsulant. The device is configured to be rolled to form a guiding tube having two open ends and to be placed at a damaged portion of a nerve. When the device is illuminated by light, a photovoltage exists between the first conductive layer and the second conductive layer for producing an electric current, so as to stimulate neural regeneration and repair the damaged portion of a nerve.

13 Claims, 3 Drawing Sheets

DEVICE FOR STIMULATING NEURAL REGENERATION AND FABRICATION METHOD THEREOF

CROSS-REFERENCES TO RELATED APPLICATIONS

This application claims under 35 U.S.C. §119(a) the benefit of Taiwanese Application No. 101118472, filed May 24, 2012, the entire contents of which is incorporated herein by reference.

BACKGROUND OF THE INVENTION

1. Field of the Invention

The present invention relates to devices for stimulating neural regeneration and fabrication methods thereof, and, more particularly, to a device having a photovoltaic component for stimulating neural regeneration electrically and a fabrication method thereof.

2. Description of Related Art

Due to many paralysis patients resulting from damaged spinal cord or nerves, there is an urgent need to repair a damaged portion of a nerve. However, human neural cells are poorly regenerated with respect to other cells, such that the efficiency of neural treatment is poor.

In the current therapy, patients are treated with autologous nerve grafts. However, the donor nerve grafts, which are usually taken from a part of the body, would lose their functions.

Therefore, it is developed in the field to find a scaffold or nerve guidance channel for neural regeneration, directing regeneration of neural cells and repairing a damaged portion of a nerve. It has been found that electrical stimulation would significantly enhance neural generation, so as to improve treatment efficiency and shorten therapy time.

U.S. Pat. No. 4,308,868 disclosed a flexible electrode array for stimulating neural regeneration. However, the device uses a watch-type disc battery, and the battery material is not suitable for being implanted into human body owing to its toxicity. In addition, U.S. Pat. No. 5,030,225 disclosed electrically-charged nerve guidance channels, which have no need to be further electrically charged. However, it is limited to enhance neural regeneration without continuous electrical stimulation.

Hence, it is an urgent issue to develop a device for being implanted in human bodies without the need of an external power supply.

SUMMARY OF THE INVENTION

In order to overcome the drawbacks in the conventional technology, the present invention provides a device for stimulating neural regeneration electrically and a fabrication method thereof. The device can be implanted into a body and driven by in vitro light, so as to further stimulate neural regeneration.

In accordance with the present invention, the device includes a photovoltaic component having a substrate, a first conductive layer, an active layer and a second conductive layer stacked in sequence; and an encapsulant for encapsulating the photovoltaic component to form the device, with a portion of the first conductive layer and that of the second conductive layer exposed from the encapsulant, wherein the device is configured to be placed at a damaged portion of a nerve, and when the device of the device is illuminated by light, a voltage difference exists between the first conductive layer and the second conductive layer for producing an electric current, so as to stimulate neural regeneration or neurite outgrowth and treat the damaged portion of the nerve.

In one embodiment of the present invention, the device is rolled as a guiding channel having two open ends, and the guiding channel is configured to receive the damaged portion of the nerve. In another embodiment of the present invention, the device is in a form of a scaffold for being disposed at the damaged portion of the nerve.

In addition, the encapsulant for encapsulating the photovoltaic component is biocompatible. The first conductive layer of the photovoltaic component includes a first electrode layer and a conductive polymer layer formed on the first electrode layer. The active layer is formed by a mixed semiconductor material of an n-type semiconductor material (electron-acceptor) and a p-type semiconductor material (electron-donor). The second conductive layer of the photovoltaic component includes a second electrode layer and an electrical connection layer formed on the second electrode layer.

In accordance with the present invention, a fabrication method of a device for stimulating neural regeneration includes the steps of: (1) forming a photovoltaic component having a substrate, a first conductive layer, an active layer and a second conductive layer stacked in sequence; (2) encapsulating the photovoltaic component to form the device with a portion of the first conductive layer and a portion of the second conductive layer exposed from the encapsulant; and (3) rolling the device to form a guiding channel having two open ends, wherein the device is configured to be placed at a damaged portion of a nerve, and when the photovoltaic component of the device is illuminated by light, a voltage difference exists between the first conductive layer and the second conductive layer for producing an electric current, so as to stimulate neural regeneration and treat the damaged portion of the nerve.

In comparison with the prior art, the device of the present invention can be implanted into a body of an organism without being connected to an external battery or other energy source. Hence, the device of the present invention has no need for multiple surgical procedures, and further can provide stable electrical stimulation for neural regeneration.

DETAILED DESCRIPTION OF THE PREFERRED EMBODIMENTS

The detailed description of the present invention is illustrated by the following specific examples. Persons skilled in the art can conceive the other advantages and effects of the present invention based on the disclosure contained in the specification of the present invention.

The term "a first" or "a second" described in the specification of the present invention is used for illustration but not for limiting the scope of the present invention.

Figure 1:
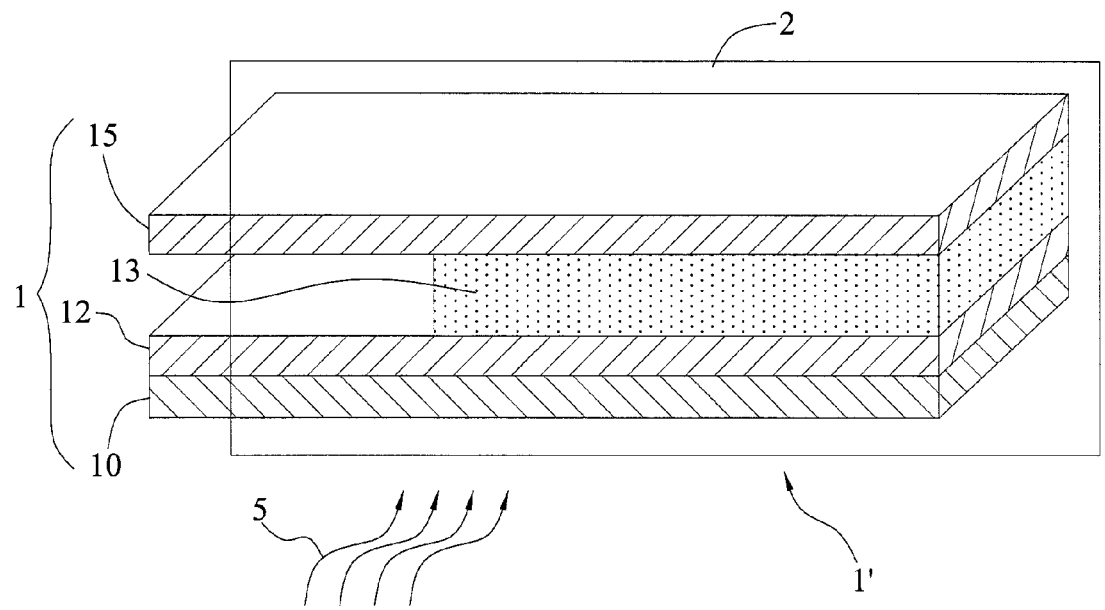
FIG. 1 is a schematic view showing a device for stimulating neural regeneration and/or neurite outgrowth according to the present invention.

FIG. 1 shows a device 1' for stimulating neural regeneration and/or neurite outgrowth according to the present invention. The device 1' includes a photovoltaic component 1 and an encapsulant 2.

The photovoltaic component 1 includes a substrate 10, a first conductive layer 12, an active layer 13 and a second conductive layer 15 stacked in sequence. The substrate 10 is a flexible substrate. The first conductive layer 12 and the second conductive layer 15 are made of a conductive polymer. The active layer 13 is made of a mixed semiconductor material of an n-type semiconductor material (such as [6,6]-phenyl-C61-butyric acid methyl ester, PCBM) and a p-type semiconductor material (such as poly(3-hexylthiophene), P3HT).

The encapsulant 2 such as a biocompatible plastic encapsulant is used for encapsulating the photovoltaic component 1 and exposing a portion of the first conductive layer 12 and a portion of the second conductive layer 15, so as to form the device 1'. As shown in FIG. 1, the dotted line indicates the encapsulation range of the encapsulant 2.

The device 1' is placed at a damaged portion of a nerve. When the photovoltaic component 1 of the device 1' is illuminated by light 5 (for example, near-infrared photons passing through human tissues to the photovoltaic component implanted in the human body), a photovoltage exists between the first conductive layer 12 and the second conductive layer 15 so as to produce an electric current for stimulating neural regeneration and thus repairs the damaged portion of the nerve.

Figure 2:
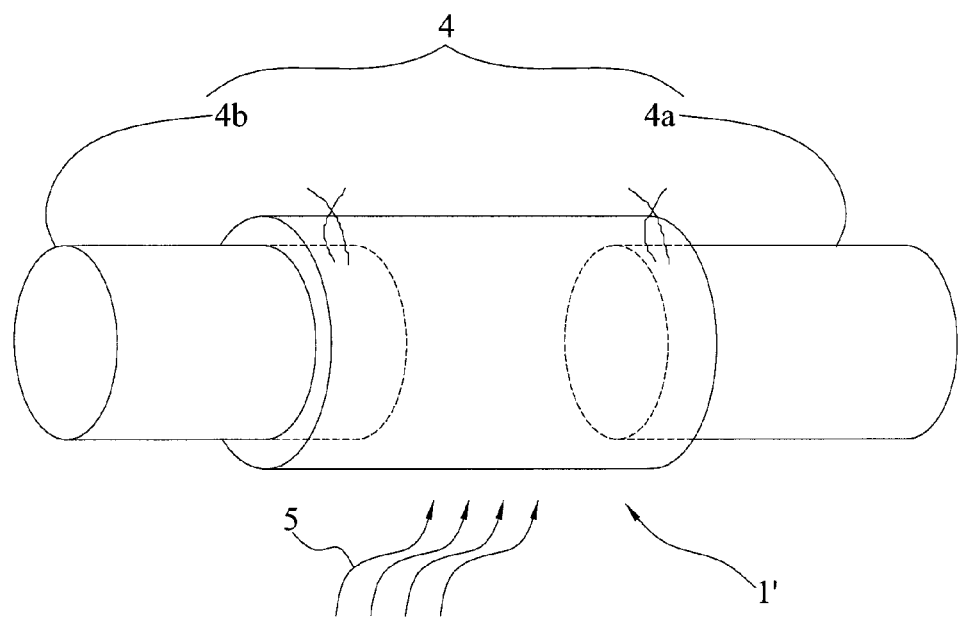
FIG. 2 is a schematic view showing a device for stimulating neural regeneration connected to a cut nerve according to the present invention.

The device 1' may be a guiding channel or a scaffold. Specifically, the device 1' is rolled to form a guiding channel having two open ends for receiving the damaged portion of the nerve. FIG. 2 shows the device 1' rolled as a guiding channel having two open ends. As shown in FIG. 2, a nerve 4 is cut into nerve segments 4a and 4b, the nerve segments 4a and 4b are respectively introduced into the guiding channel via the two open ends of the device 1', and the severed nerve is reconnected via the guiding channel upon the surgery to assist the neural regeneration. Generally, if a large part of a nerve is cut and the nerve is directly reconnected via surgery, most functions of the nerve would gradually lose. Therefore, the two nerve segments 4a and 4b need to be reconnected via the guiding channel. If there is no such guiding channel, neural cells would grow randomly and the transected nerve ends are hard to be repaired.

In addition, there is no limitation to the shape of the device 1' according to the present invention as long as the damaged/cut portion of the nerve may be received in the guiding channel. Thus, when the photovoltaic component of the device 1' is illuminated by the light 5, a photovoltage exists between the first conductive layer 12 and the second conductive layer 15 so as to stimulate the growth of the nerve 4 and to connect the nerve segments 4a and 4b.

The device 1' may be a scaffold for connecting the two nerve segments and stimulating the growth of the nerve, and there is no limitation to the shape of the scaffold. As shown in FIG. 1, the device 1' is placed between the nerve segments 4a and 4b for connecting the nerve segments 4a and 4b. The nerve segments 4a and 4b are respectively connected to the first conductive layer 12 and the second conductive layer 15 via a biocompatible adhesive, and thus there is a photovoltage between the first conductive layer 12 and the second conductive layer 15 to stimulate neural regeneration. Alternatively, the nerve segments 4a and 4b are connected to the device 1' via stitching, and thus the nerve is attached to the device for stimulating neural regeneration in the present invention.

Figure 3:
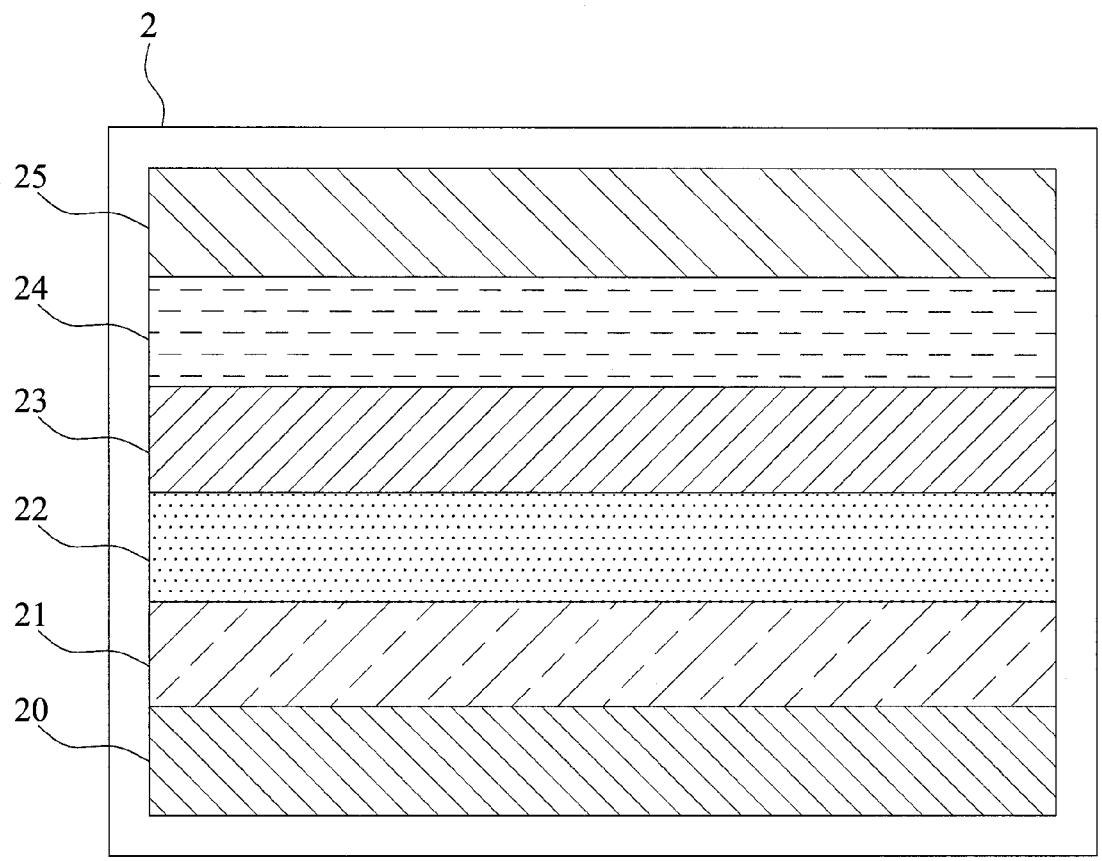
FIG. 3 is a schematic view showing a section view of a device for stimulating neural regeneration according to the present invention.

FIG. 3 shows a photovoltaic component in a device for stimulating neural regeneration according to an embodiment of the present invention. In this embodiment, the photovoltaic component includes a substrate 20, a first electrode layer 21, a conductive polymer layer 22, an active layer 23, a second electrode layer 24 and an electrical connection layer 25 stacked in sequence.

The first electrode layer 21 and the conductive polymer layer 22 may form the first conductive layer 12 shown in FIG. 1, and the material of the first electrode layer 21 may include indium tin oxide or indium zinc oxide. The active layer 13 is made of a mixed semiconductor material of an n-type semiconductor material (such as [6,6]-phenyl-C61-butyric acid methyl ester) and a p-type semiconductor material (such as poly(3-hexylthiophene)). The second electrode layer 24 and the electrical connection layer 25 form the second conductive layer 15 shown in FIG. 1. The second electrode layer 24 may include calcium, and the electrical connection layer 25 may include aluminum.

Figure 4:
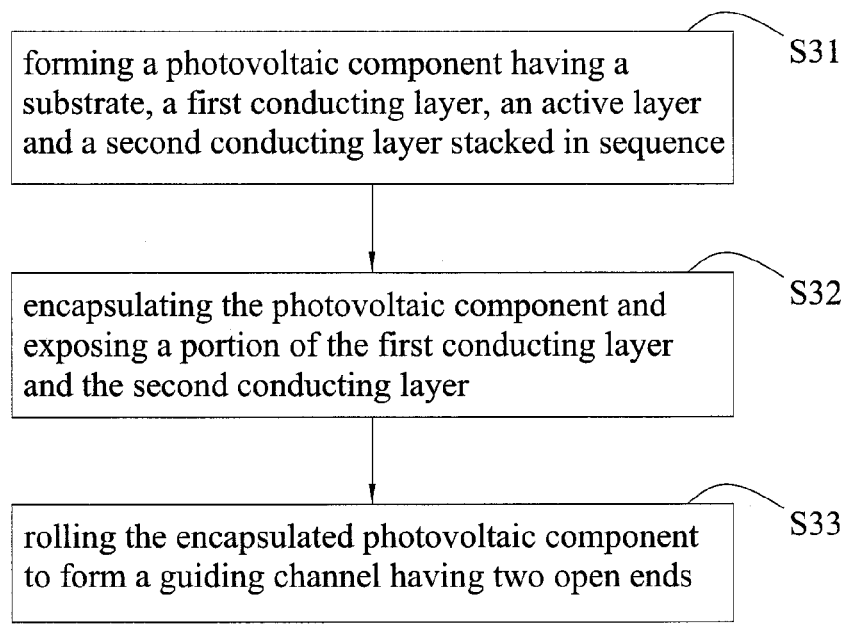
FIG. 4 is a flow chart showing a fabrication method of a device for stimulating neural regeneration according to the present invention.

FIG. 4 shows a fabrication method of a device for stimulating neural regeneration according to the present invention. In step S31, a photovoltaic component having a substrate 10, a first conductive layer 12, an active layer 13 and a second conductive layer 15 stacked in sequence is formed. For example, a flexible substrate 20 is formed thereon with a first electrode layer 21 and then applied with a conducting polymer layer 22, such that the first conductive layer is formed on the substrate 20. Then, an active layer 23 (e.g., an organic semiconductor layer) is deposited on the first conductive layer. Upon annealing, a second electrode layer 24 and an electrical connection layer 25 are formed on the active layer 23 by thermal evaporation to form the second conductive layer. The cathode may be made of calcium, and aluminum is used as the wire connected to an external circuit and protects the calcium from being oxidized by water and oxygen.

In step S32, the biocompatible plastic is used for encapsulating the photovoltaic component and exposing a portion of the first conductive layer and a portion of the second conductive layer.

In step S33, the device 1' is rolled to form a guiding channel having two open ends. The guiding channel is placed at a damaged portion of a nerve. When the photovoltaic component of the device 1' is illuminated by light, there is a photovoltage between the first conductive layer and the second conductive layer to stimulate the growth of the nerve and thus to treat the damage portion of the nerve.

Figure 5:
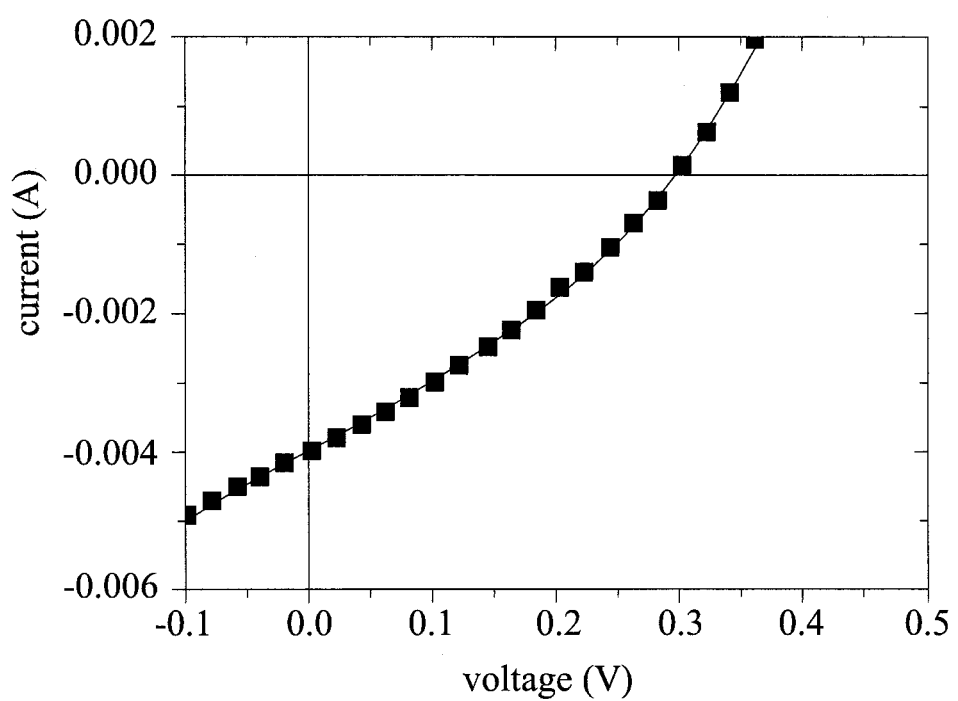
FIG. 5 is a chart showing the current density and voltage of the photovoltaic component in the device for stimulating neural regeneration illuminated by 980 nm laser according to the present invention.

FIG. 5 is a chart showing the current density and voltage of the photovoltaic component in the device for stimulating neural regeneration illuminated by 980 nm laser according to the present invention. As shown in FIG. 5, when the energy of the incident light is 24 mW, the photovoltaic component has the open-circuit voltage of 0.29 V, the short-circuit current of 0.004 mA, the fill factor of 0.31, and the energy conversion efficiency of 0.0016%. Hence, the photovoltaic component driven by red or near-infrared (wavelength about 500-1500 nm) photons has significant photovoltaic effect in the present invention.

Since the neural regeneration is slow, the device for implantation needs to have convenient power supply and needs to be comfortable. In the present invention, the device for stimulating neural regeneration has flexibility and biocompatibility, and thus can be implanted into a body of an organism and self-powered due to the photovoltaic effect driven by in vitro near-infrared photons, so as to stimulate neural regeneration and speed the neural recovery. In the present invention, there is no need to connect the electrode to an external power supply, so as to reduce the number of surgery and help the patient relief his pain.

The invention has been described using exemplary preferred embodiments. However, it is to be understood that the scope of the invention is not limited to the disclosed arrangements. The scope of the claims, therefore, should be accorded the broadest interpretation, so as to encompass all such modifications and similar arrangements.

The invention claimed is:

1. A device for stimulating neural regeneration, comprising:
   a photovoltaic component having a substrate, a first conductive layer, an active layer and a second conductive layer stacked in sequence; and
   an encapsulant for encapsulating the photovoltaic component with a portion of the first conductive layer and a portion of the second conductive layer exposed from the encapsulant, wherein the device is configured to be placed at a damaged portion of a nerve, and when the encapsulated photovoltaic component of the device is illuminated by red or near-infrared light, the encapsulated photovoltaic component has an energy conversion efficiency equal to or greater than 0.0016% at a wavelength of 500 to 1500 nm, and a photovoltage exists between the first conductive layer and the second conductive layer for producing an electric current, so as to stimulate neural regeneration of and repair the damaged portion of the nerves.

2. The device of claim 1, configured to be rolled as a guiding channel having two open ends, so as for the guiding channel to receive the damaged portion of the nerve.

3. The device of claim 1, the device is a scaffold to be disposed at the damaged portion of the nerve.

4. The device of claim 1, wherein the first conductive layer comprises a first electrode sub-layer formed on the substrate and a conductive polymer sub-layer formed on the first electrode sub-layer.

5. The device of claim 4, wherein the first conductive layer is made of indium tin oxide or indium zinc oxide.

6. The device of claim 1, wherein the active layer is made of a mixed semiconductor material of an n-type semiconductor material and a p-type semiconductor material.

7. The device of claim 6, wherein the n-type semiconductor material includes phenyl C61-butyric acid methyl ester, and the p-type semiconductor material includes poly(3-hexylthiophene).

8. The device of claim 1, wherein the second conductive layer comprises a second electrode sub-layer formed on the active layer and an electrical connection sub-layer formed on the second electrode sub-layer.

9. The device of claim 8, wherein the second electrode sub-layer includes calcium, and the electrical connection sub-layer includes aluminum.

10. The device of claim 1, wherein the encapsulant is a biocompatible plastic.

11. A fabrication method of a device for stimulating neural regeneration, comprising the steps of:
    forming a photovoltaic component having a substrate, a first conductive layer, an active layer and a second conductive layer stacked in sequence;
    encapsulating the photovoltaic component to form the device with a portion of the first conductive layer and a portion of the second conductive layer exposed from an encapsulant, wherein when the encapsulated photovoltaic component is illuminated by red or near-infrared light, the encapsulated photovoltaic component has an energy conversion efficiency equal to or greater than 0.0016% at a wavelength of 500 to 1500 nm; and
    rolling the device to form a guiding channel having two open ends, so as for the device to be placed at a damaged portion of a nerve, and such that when the device is illuminated by red or near-infrared light, a photovoltage exists between the first conductive layer and the second conductive layer for producing an electric current, so as to stimulate neural regeneration and repair a damaged portion of a nerve.

12. The fabrication method of claim 11, wherein the first conductive layer is formed by forming a first electrode sub-layer and a conducting polymer sub-layer stacked on the first electrode sub-layer.

13. The fabrication method of claim 11, wherein the second conductive layer is formed by forming a second electrode sub-layer and an electrical connection sub-layer stacked on the second electrode sub-layer.

* * * * *